United States Patent [19]

Van der Salm

[11] Patent Number: Plant 5,643

[45] Date of Patent: Jan. 21, 1986

[54] LILY PLANT: UNIQUE

[76] Inventor: Gerardus C. Van der Salm, Rte. 1, Box 422, Woodland, Wash. 98674

[21] Appl. No.: 551,272

[22] Filed: Nov. 14, 1983

[51] Int. Cl.[4] ..... A01H 5/00
[52] U.S. Cl. ..... Plt./68
[58] Field of Search ..... Plt./68

*Primary Examiner*—James R. Feyrer
*Attorney, Agent, or Firm*—Klarquist, Sparkman, Campbell, Leigh & Whinston

[57] ABSTRACT

A new variety of Asiatic hybrid lily plant having a flower with a deep greyed-orange central region, generally white petals with a diffused greyed-orange perimeter and a more concentrated greyed-orange tip region.

2 Drawing Figures

1

This present invention relates to a new and distinct variety of lily classified botannically as a lilium hybrid and commercially as an upright Asiatic hybrid. This new lily, which I call "Unique", was originated by me by crossing an unnamed variety with an unnamed variety.

My primary objective in breeding lilies, which resulted in the origination of this new variety, was to produce brilliantly-colored, upright-flowering lily cultivars, which would perform well when forced into flower, in addition to satisfactorily meeting the requirements of vigor, disease resistance, and rapid natural propagation in field growth.

This objective was substantially achieved in my new variety, along with other desirable improvements, as evidenced by the following unique combination of characteristics which are outstanding in the new variety and which distinguish it from other varieties of which I am aware:

1. Healthy and vigorous growth; and
2. A flower with a deep greyed-orange central region, generally white petals with a diffused greyed-orange perimeter and a more concentrated greyed-orange tip region.

My new variety of lily plant has been asexually reproduced at my direction at the W. C. J. Van Der Salm and Sons Bulb Farm in Julianadorp, Holland and successive generations of my new variety, produced by scaling of bulbs, have demonstrated that the foregoing characteristics and distinctions are true to form, are firmly fixed, and are transmitted through succeeding propagations.

The accompanying illustration shows a typical specimen of the flower, buds, and leaves of my new variety, depicted in color as nearly true as it is reasonably possible to make the same in a color illustration of this character.

The following is a detailed description of my new lily cultivar with color and terminology in accordance with The Royal Horticultural Society Colour Chart, except where ordinary dictionary significance of color is indicated.

Parentage:
- *Seed parent.*—Unnamed variety.
- *Pollen parent.*—Unnamed variety.

Classification:
- *Botannical.*—Lilium hybrid.
- *Commercial.*—Asiatic hybrid.

2

THE PLANT

Form: *Bulbous monocotyledon.*
Height: 70–90 cm (28–35")
Growth: Vigorous, with considerable strength.
Foliage:
- *Quantity.*—Abundant, about 100–140 leaves per stem.
- *Size of leaves.*—6–10 cm ($2\frac{1}{2}$–4") long and 1–1.6 cm ($\frac{3}{8}$–$\frac{5}{8}$") wide.
- *Shape of leaves.*—Linear with acuminate tip.
- *Texture of leaves.*—Leaves entire (not serrated), glabrous.
- *Color of leaves.*—Medium green.
- *Ribs and veins of leaves.*—Typical monocotyledonous venation.

INFLORESCENCE

Well-spaced pyramidal raceme with no secondary buds. Bulbs 10–12 cm in circumference produce an average of 9–10 buds; bulbs 12–14 cm in circumference produce 12–16 buds.

Peduncle and pedicels; Glabrous.
Sepals: Slightly pubescent.
Strength of inflorescence: Very strong, long life.

THE BUDS

Size: 8.3–10 cm ($3\frac{1}{4}$–4") long.
Form: Lanceolate with obtuse tip; typical of Asiatic lilies.

THE FLOWER

Size: Flower diameter is 15–18 cm (6–7").
Shape when bloom first opens: Bowl-shaped with recurving tips. Tepals recurve more as flower ages.
Tepal arrangement: Typical of the genus Lilium, with 6 entire, imbriated tepals.
- *Color, base of tepal.*—Deep greyed-orange (like R.H.S. 176A).
- *Color, body of tepal.*—Generally white with a diffused greyed-orange perimeter (like R.H.S. 176A) and a more concentrated greyed-orange tip region (like R.H.S. 176A).

Tepal duration: Tepals remain on individual flowers 5–7 days, stem has flowers with tepals adhering for about 3 weeks. Tepals fall as flower ages.
Pedical: Sturdy and wiry; slight ascending.
- *Length.*—10–12 cm (4–5").

*Color.*—Greyed-orange.

Fragrance: None.

THE REPRODUCTIVE ORGANS

Stamens and anthers: Typical of genus Lilium. 6 Versatile anthers hang (singly) from 6 filaments.

Pollen: Brown.

Pistil: One, typical of genus Lilium.

Stigma: Tiny, three-lobed.

Ovary: Typical of genus Lilium. Superior, single, 6-chambered ovary.

THE BULBS

Color of bulbs: White.

Size of bulbs: Usual commercial size is about 12–20 cm (5–8″) in circumference; bulbs can reach much larger size if desired.

I claim:

1. A new and distinctive variety of Asiatic hybrid lily plant substantially as herein shown and described, characterized by its vigorous growth and a flower with a deep greyed-orange central region, generally white petals with a diffused greyed-orange perimeter and a more concentrated greyed-orange tip region.

* * * * *

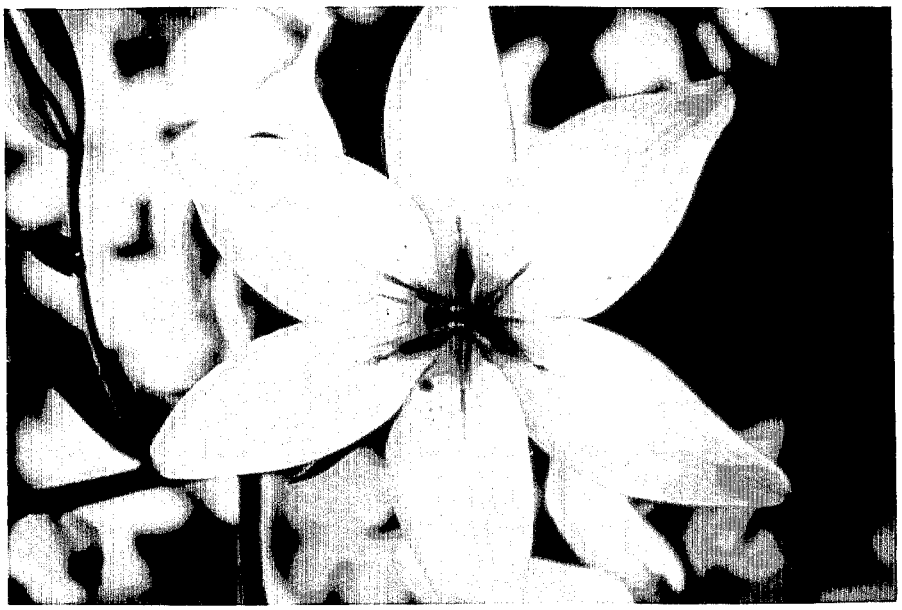
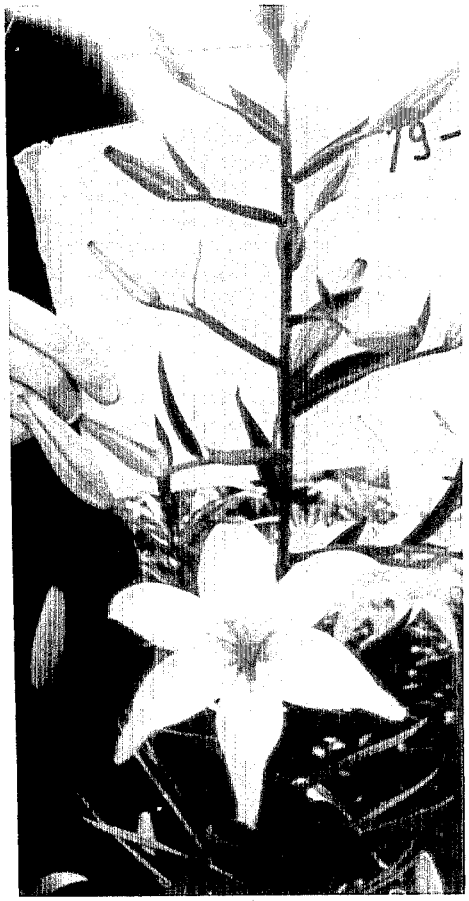
79-